United States Patent [19]

Dettmar et al.

[11] Patent Number: 5,286,492
[45] Date of Patent: Feb. 15, 1994

[54] **METHOD OF TREATMENT OF *HELIOBACTER PYLORI* INFECTIONS WITH TRICLOSAN**

[75] Inventors: Peter W. Dettmar, Welwick; John G. Lloyd-Jones, Cottingham, both of United Kingdom

[73] Assignee: Reckitt & Colman Products Limited, London, United Kingdom

[21] Appl. No.: 693,598

[22] Filed: Apr. 30, 1991

[30] Foreign Application Priority Data

May 3, 1990 [GB] United Kingdom ............... 9010039

[51] Int. Cl.$^5$ .................. A61K 9/58; A61K 9/60; A61K 9/62; A61K 9/28
[52] U.S. Cl. .................. 424/458; 424/464; 424/465; 424/457; 424/466; 424/494; 424/496; 424/497
[58] Field of Search ............. 424/451, 456, 464, 465, 424/452, 489

[56] References Cited

FOREIGN PATENT DOCUMENTS

| | | |
|---|---|---|
| 0205282 | 12/1986 | European Pat. Off. . |
| 0206625 | 12/1986 | European Pat. Off. . |
| 0206626 | 12/1986 | European Pat. Off. . |
| 0206627 | 12/1986 | European Pat. Off. . |
| 0219912 | 4/1987 | European Pat. Off. . |
| 0220890 | 5/1987 | European Pat. Off. . |
| 0282131 | 9/1988 | European Pat. Off. . |
| 0282132 | 9/1988 | European Pat. Off. . |
| WO86/05981 | 10/1986 | PCT Int'l Appl. . |
| WO89/03219 | 4/1989 | PCT Int'l Appl. . |
| 1022744 | 2/1964 | United Kingdom . |
| 1024022 | 2/1964 | United Kingdom . |
| 1038185 | 2/1964 | United Kingdom . |
| 1485676 | 9/1977 | United Kingdom . |
| 2015875 | 9/1979 | United Kingdom . |

OTHER PUBLICATIONS

*Patent Abstracts of Japan*, vol. 14, No. 126, Mar. 9, 1990.
Rauws et al., *Gastroenterology*, 1988, 94:33–40.
Vaira et al., *Current Opinion in Gastroenterology*, 1989, 5:817–823.
McNulty et al., *Antimicrobial Agents and Chemotherapy*, Dec. 1985, 28,6,837–838.

*Primary Examiner*—Thurman K. Page
*Assistant Examiner*—N. Levy
*Attorney, Agent, or Firm*—Bacon & Thomas

[57] ABSTRACT

A method for the treatment of gastrointestinal disorders associated with *Helicobacter pylori* infections which comprises administering to a patient an orally effective amount of triclosan is disclosed. The triclosan may be administered in the form of powders, granules, spheroids or liquids, or in unit dosage form as capsules or tablets containing 1 to 100 mg, preferably 10 to 60 mg, of triclosan. The triclosan may also be administered in gastric sustained release medicaments either as raft forming tablets or liquids, optionally to be co-administered with a solid pharmaceutically acceptable carboxylic acid or acid salt, or as mucoadherent-coated granules or spheroids.

23 Claims, No Drawings

METHOD OF TREATMENT OF *HELIOBACTER PYLORI* INFECTIONS WITH TRICLOSAN

This invention relates to the preparation of a medicament for the treatment of gastrointestinal disorders associated with *Helicobacter pylori* infections.

The relationship between peptic ulcer disease and gastritis has been recognised for several decades. The relationship between gastritis and infection with *Helicobacter pylori* (formerly *Campylobacter pylori*), first demonstrated by Warren and Marshal in 1983, is now equally well established, see Vaira et al (Current Opinion in Gastroenterology 1989, 5: 817-823). Given this connection it is now being recognised that treatments of gastritis and peptic ulcer must be capable of removing the associated *Helicobacter pylori* infections.

A number of different treatment regimens have been proposed to treat *Helicobacter pylori* infections. European Patent applications No. 206626 and 206627 (Marshall) describe the use of bismuth salts whilst EP 206625 (Marshall) and WO 86/05981 (Borody) describe the use of a combination of bismuth with a single antibiotic for the treatment of *Helicobacter pylori*. However, bismuth alone achieves low (30 to 70%) initial clearance rates for *Helicobacter pylori* and recurrence of the infection approaches 100% by twelve months post therapy. Bismuth together with a single antibiotic, namely amoxicillin, appears to be relatively effective as a short term means of reducing the symptoms but it is now clear that the use of bismuth together with a single antibiotic frequently fails to eradicate the infection and has a high rate of reinfection (Rauws, Erik A. J. et al, Gastroenterology, 1988, 94: 33-40). WO 89/03219 (Borody) describes the use of a combination of bismuth, a first antimicrobial agent and a second antimicrobial agent. This treatment regimen is not only complicated and expensive but still has unacceptably high relapse rates.

A second approach to combination therapy uses histamine-$H_2$ receptor blocking anti-secretory agents. European Patent applications 282132 and 282131 (Proctor and Gamble) describe the use of $H_2$ antagonists in combination with bismuth or Campylobacter inhibiting anti-microbial agents. This approach has still led to high relapse rates and may lead to many of the undesirable side effects of the individual treatment components.

European Patent application No. 219912 (Norwich Eaton) describes the use of nitrofurantoin as a monotherapy for the treatment or prophylaxis of infectious gastrointestinal disorders caused or mediated by Campylobacter-like organisms. This approach has been replaced in common practice by more complex duo or triple therapy.

There is still a requirement for an effective monotherapy of gastrointestinal disorders associated with *Helicobacter pylori*.

We have now investigated the in vitro activity of various non-antibiotic antimicrobial agents versus *Helicobacter pylori*.

Triclosan (2-hydroxy-4,2',4'-trichloro-diphenyl ether) is described and claimed, along with various formulations, in GB Patents 1022744, 1024022 and 1038185, published in 1966. Whilst GB 1022744 claims that triclosan may be used for "oral administration to disinfect the intestinal and urinary tracts" very few details are given, and no specific infections or conditions are mentioned. Since these patents were published Applicant is not aware of any publications suggesting the use of triclosan in the treatment of any gastrointestinal diseases, nor have there been any suggestions that triclosan may have activity against gastrointestinal infections with *Helicobacter pylori* or any of the associated disease conditions.

According to the present invention there is provided a method for the treatment of gastrointestinal disorders associated with *Helicobacter pylori* infections which comprises administering to a patient an orally effective amount of triclosan.

The effective oral dose of triclosan will depend upon the severity of the condition to be treated. Generally the dosage employed will fall within the range of 1 to 200 mg and for most patients will fall within the range 10 to 100 mg, for example 25 mg. The frequency of dosing will again be dependent upon the severity of the condition to be treated and its sensitivity to the treatment, the dosing normally being up to three times a day.

The medicaments will be for oral administration and may be in the form of powders, granules, spheroids, tablets, capsules, solutions or suspensions.

For ease of administration and for accuracy in dosing, the medicament may be prepared in unit dosage forms. Thus in the case of powders, granules or spheroids they may be conveniently packed into sachets, each unit containing, from 1 to 100 mg (preferably 10 to 60 mg) triclosan. In the case of tablets or capsules each unit will contain from 1 to 100 mg (preferably 10 to 60 mg) triclosan.

The medicament in the form of granules may be prepared by standard methods such as wet or dry granulation (slugging). They may be effervescent or non-effervescent to be mixed with a suitable quantity of water for administration as a drink. They may also be chewable granules.

The medicaments in the form of spheroids may be prepared by the following method. The triclosan and a carrier (for example microcrystaline cellulose) plus any other excipients are mixed with a sufficient quantity of water to form a 'plastic' wet mass. The mass is extruded into cylinders of uniform diameter and equal length. The extrudates are rolled into spheres using a spheroniser and then dried, preferably in a fluid bed dryer.

The medicaments in the form of powders may be prepared by blending the triclosan and one or more pharmaceutically acceptable excipients such as bulking agents/diluents.

The medicaments in the form of tablets may be prepared by standard methods such as granulation or direct compression. They may be buffered and effervescent or non-effervescent.

The medicaments in the form of capsules may be prepared by standard methods such as filling powders, granules or spheroids into hard gelatine capsules or adding triclosan to melted pharmaceutically acceptable excipients before filling into capsules.

The medicaments in the form of solutions or suspensions may be prepared by mixing the components with a liquid such as water. Conveniently the liquid formulations will contain 1 to 100 mg of triclosan in 5 to 20 ml. They may include pharmaceutically acceptable conventional excipients such as suspending agents, buffer systems etc. In order to protect the medicaments against microbial deterioration it is preferable to include a preservative. A suitable system is a combination of methyl- and propyl- para-hydroxybenzoate (methyl and propyl parabens).

The medicaments may also include one or more of a colourising, sweetening or flavouring agent.

In another aspect of the invention the medicaments may be formulated as gastric sustained release compositions, having prolonged residence time within the stomach and continuously releasing triclosan during that time. In this aspect the medicaments may be formulated so as to produce floating alginate rafts within the stomach, or as mucoadherant-coated granules or spheroids.

Medicaments formulated so as to produce floating alginate rafts within the stomach may be in solid single dosage form as tablets, or in liquid form.

In the form of tablets the alginate containing gastric sustained release compositions of triclosan will comprise 200 to 600 mg of alginic acid and/or a salt thereof, preferably a sodium, potassium or magnesium salt; 50 to 250 mg of a sodium or potassium carbonate or bicarbonate salt; 1 to 100 mg, preferably 10 to 60 mg, triclosan; and optionally up to 100 mg calcium carbonate. The compositions may also contain standard tableting excipients known in the art, such as soluble fillers, binders, lubricants and flavours. The tablets may be produced by standard procedures such as direct compression or by wet or dry granulation followed by tablet compression.

In the form of liquids the alginate containing gastric sustained release compositions of triclosan will comprise an aqueous medium containing 0.1 to 2% w/v triclosan; 1 to 8% w/v sodium or potassium alginate; 1.3 to 6.5% w/v sodium or potassium carbonate or bicarbonate salt; 0.5 to 4% calcium carbonate and optionally 0.3 to 1.7% w/v of a suspending agent, preferably carbomer. These liquid compositions may also contain standard excipients known in the art such as preservatives, flavouring and colouring agents. The alginate containing liquids may be produced by dispersing all of the ingredients except carbomer in water. If carbomer is used it will be added to the dispersion as a neutralised suspension in water.

When the alginate compositions described above come into contact with the, normally, acid conditions of the stomach the carbonate or bicarbonate salts produce effervescence, which aerates the raft structure formed by the alginates, causing it to float. It has, however, been noted that in some patients suffering from *Helibacter pylori* infections the pH of the stomach contents may be elevated (possibly to as high as pH6) reducing effervescence and, consequently, reducing the ability of the rafts to float. Floating rafts may still be formed in such patients however either by, in the case of tablet compositions, further including a pharmaceutically acceptable, solid carboxylic acid, or an acid salt thereof in a sufficient amount to neutralise between one quarter and all of the carbonate and/or bicarbonate of the composition; or, in the case of tablet or liquid compositions, co-administering such an acid or acid salt. A suitable acid is citric acid.

Mucoadherent-coated granules or spheroids may be produced by forming triclosan containing granules or spheroids as described above, and coating them with one or more known mucoadherent polymers such as carboxymethylcellulose or sodium carboxymethylcellulose, carbomer (especially carbomer 934P), tragacanth, sodium alginate, methylcellulose, hydroxyethylcellulose, poly(ethylene oxide) or hydroxypropylmethylcellulose. The coating may be carried out by any conventional technique, for example spray coating. Once coated and dried the granules or spheroids may be filled into sachets or gelatine capsules or, if sufficiently robust microadherent coatings have been used, compressed to form tablets.

The invention is illustrated by the following examples.

EXAMPLE 1

Tablet

A preparation in the form of tablets was prepared according to the following formula

| Triclosan | 200 g |
|---|---|
| Microcrystalline cellulose | 1000 g |
| Magnesium stearate | 6 g |

The materials were blended together and compressed into tablets using 8 mm diameter concave punches. Individual tablets had a weight of 301.5 mg and contained 50 mg triclosan.

EXAMPLE 2

Suspension

A preparation in the form of a suspension was prepared according to the following formula

| Triclosan | 1.0% w/v |
|---|---|
| Sodium carboxymethylcellulose | 3.0% w/v |
| Propyl parabens | 0.06% w/v |
| Methyl parabens | 0.14% w/v |
| Peppermint flavour | 0.1% w/v |
| Sodium saccharin | 0.05% w/v |
| Water to | 100% |

The triclosan, parabens, flavouring and saccharin were dispersed in the bulk of the water. The sodium carboxymethylcellulose was added and stirred vigorously until dissolved. Water was added to bring the suspension to final volume and the suspension was mixed until it was homogenous.

EXAMPLE 3

Buffered tablets

A preparation in the form of buffered tablets was prepared according to the following formula

| Triclosan | 50 g |
|---|---|
| Sodium carbonate | 300 g |
| Microcrystalline cellulose | 600 g |
| Modified cellulose gum | 30 g |
| Magnesium stearate | 5 g |

The ingredients were blended together and then compressed using 13 mm diameter normal concave punches to a weight of 985 mg. Each tablet contained 50 mg of triclosan.

EXAMPLE 4

Capsules

A preparation in the form of capsules was prepared according to the following formula

| Triclosan | 150 g |
|---|---|
| Polyethyl glycol 6000 | to 1050 g |

The polyethylene glycol was melted and the triclosan was added and stirred until dissolved. The melt was dosed into appropriately sized hard gelatine capsules such that each capsule contained 10, 50 or 100 mg triclosan.

EXAMPLE 5

Solution

A preparation in the form of a solution was prepared according to the following formula

| Triclosan | 1% w/v |
|---|---|
| Propylene glycol | 20% w/v |
| Polyethylene glycol 300 | 3% w/v |
| Propyl paraben | 0.0375% w/v |
| Methyl paraben | 0.09% w/v |
| Flavour | qs |
| Glycerol | to 100% |

The propylene glycol and polyethylene glycol were mixed and the triclosan was added and stirred until dissolved. The remaining ingredients were added and stirred until dissolved.

EXAMPLE 6

Effervescent tablets

A preparation in the form of effervescent tablets was prepared according to the following formula

| Triclosan | 50 g |
|---|---|
| Sodium carbonate | 100 g |
| Citric acid | 250 g |
| Sodium bicarbonate | 400 g |
| Sorbitol direct compression grade | 1000 g |
| Maltodextrin | 200 g |
| Peppermint flavour | 50 g |
| Sodium saccharin | 25 g |
| Magnesium stearate | 10 g |

The citric acid, sodium bicarbonate and 200 g of the sorbitol were mixed in a planetary mixer and granulated with a small amount of water. The granules were dried in a fluid bed dryer and then passed through a 780 μm mesh sieve. The remaining ingredients were added and blended together by tumble mixing. The mixture was compressed using 18 mm punches to a final tablet weight of 2085 mg. Each tablet contained 50 mg triclosan.

EXAMPLE 7

Sachets

A preparation in the form of sachets was prepared according to the following formula

| Triclosan | 100 g |
|---|---|
| Citric acid | 200 g |
| Sodium bicarbonate | 800 g |
| Sodium carbonate | 200 g |
| Sorbitol | 7000 g |
| Sodium saccharin | 100 g |
| Peppermint flavour | 200 g |

The ingredients were blended together and filled into sachets such that each sachet contained 50 mg triclosan.

EXAMPLE 8

Capsules

A preparation in the form of capsules was prepared according to the following formula

| Triclosan | 5 g |
|---|---|
| Microcrystalline cellulose | 44 g |
| Talc (sterilised) | 1 g |

The powders were blended together and filled into appropriatly sized hard gelatin capsules such that each capsule contained 10, 25 or 50 mg triclosan.

EXAMPLE 9

Alginate containing tablets

A gastric sustained release preparation in the form of alginate containing tablets was prepared according to the following formula

| | per batch g | per tablet mg |
|---|---|---|
| Triclosan | 200 | 50 |
| Alginic acid FD (Protan) | 2000 | 500 |
| Sodium bicarbonate | 680 | 170 |
| Calcium carbonate | 320 | 80 |
| Mannitol | 6092 | 1523 |
| Magnesium stearate | 100 | 25 |
| Polyvinyl pyrrolidone (PVPk30) | 400 | 100 |
| Flavour peppermint Ferm 57.279 | 200 | 50 |
| Sodium saccharin | 8 | 2 |

All the ingredients other than the triclosan, magnesium stearate and the polyvinyl pyrrolidone were sieved and mixed in a planetary mixer. The polyvinyl pyrrolidone was dissolved in 2.7 liters of isopropyl alcohol and used to granulate the mixed powders. The granules were dried in a fluid bed dryer at 70° C. for 30 minutes then sieved. The triclosan and magnesium stearate were blended into the granules and the mixture was compressed using 25 mm punches to a final tablet weight of 2.5 g. Each tablet contained 50 mg triclosan.

EXAMPLE 10

Alginate containing tablets

A gastric sustained release preparation in the form of alginate containing tablets was prepared according to the following formula

| | per batch g | per tablet mg |
|---|---|---|
| Triclosan | 20.45 | 50 |
| Alginic acid LF-60 (Protan) | 204.70 | 500 |
| Sodium bicarbonate | 69.60 | 170 |
| Calcium carbonate | 32.75 | 80 |
| Citric acid | 69.60 | 170 |
| Mannitol | 623.50 | 1523 |
| Magnesium stearate | 10.25 | 25 |
| Flavour peppermint Ferm 57.279 | 20.45 | 50 |
| Sodium saccharin | 0.80 | 2 |

All the ingredients with the exception of the citric acid and magnesium stearate were sieved and mixed in a planetary mixer at a low speed setting. 250 ml of deionised water were then introduced and the mixing speed increased, mixing continued for 3 minutes. The resultant granules were dried in an oven at 100° C. for 40 minutes and then sieved. The citric acid and magnesium stearate were blended into the granules and the resultant mixture was compressed using 25 mm punches to give 2.57 g tablets each containing 50 mg triclosan.

EXAMPLE 11

Alginate containing suspension

A gastric sustained release preparation in the form of an alginate containing suspension was prepared according to the following formula

|  | per batch | % w/v |
|---|---|---|
| Triclosan | 250 | 0.5 |
| Carbomer 934P | 325 | 0.65 |
| Sodium alginate SF120 (Protan) | 750 | 1.5 |
| Sodium bicarbonate | 1335 | 2.67 |
| Calcium carbonate | 800 | 1.6 |
| Methyl paraben | 200 | 0.4 |
| Propyl paraben | 30 | 0.06 |
| 20% Sodium hydroxide (w/v) approx | 650 | 1.3 |
| Deionised water | to 50 L | to 100% |

The carbomer was fully dispersed in approximately 20 liters of the deionised water. 20% w/v sodium hydroxide was added to bring the pH to between 7.0 and 7.2. The sodium alginate was dispersed in a separate 20 liters of deionised water and the sodium bicarbonate, parabens and calcium carbonate were added and stirred until homogenous. The gelled, neutralised carbomer was added to the alginate dispersion and mixed until homogenous. The triclosan was added and mixed and the batch was adjusted to final volume with deionised water.

EXAMPLE 12

Carbomer coated spheroids

A gastric sustained release preparation in the form of capsules containing carbomer-coated spheroids was prepared according to the following formula procedure.

Spheroids were prepared according to the following formula

|  | per batch |
|---|---|
| Microcrystalline cellulose | 2500 g |
| Triclosan | 500 g |

The powders were blended for 15 minutes, following which a total of 950 ml of deionised water was added in aliquots whilst stirring continued at a slow speed. When the water had been incorporated the speed was increased for 2 minutes. The wet mass was extruded through a perforated screen of 1 mm diameter holes using a Nica extruder (Nica Systems, Sweden). The wet extrudates were spheronised using a Nica spheroniser at 650 rpm for 5 minutes. The spheroids were dried at 50° C. for 1 hour.

A coating suspension was produced according to the following formula

| Carbomer 934P | 60.0 g |
|---|---|
| Polyethylene glycol 6000 | 60.0 g |

| -continued | |
|---|---|
| Citric acid | 56.25 g |
| Deionised water | 3000.00 ml |

The citric acid and polyethylene glycol were dispersed in 2250 ml of the deionised water. The carbomer was added and dispersed by stirring at 2000 rpm. The solution was made to volume by the addition of the rest of the water.

The dried triclosan spheroids were coated with the coating suspension using an Aeromatic Strea 1 fluid bed system and a spray nozzle diameter of 1.1 mm. All of the suspension was used to coat the 3 Kg of cores.

The coated spheroids were dried and filled into hard gelatine capsules such that each capsule contained 25 mg of triclosan.

EXAMPLE 13

Sodium carboxymethylcellulose-coated spheroids

A gastric sustained release preparation in the form of capsules containing sodium carboxymethylcellulose-coated spheroids was produced according to the following procedure.

Triclosan containing spheroids were produced as described in Example 12.

A coating suspension was produced according to the following formula

| Sodium carboxymethylcellulose (low viscosity grade) | 60 g |
|---|---|
| Polyethylene glycol 6000 | 60 g |
| Deionised water | 3000 ml |

The sodium carboxymethylcellulose and polyethylene glycol were sequentially dispersed in 2400 ml of the deionised water by stirring at 2000 rpm. The solution was made up to volume by the addition of the rest of the water.

The triclosan cores were coated with the above suspension using the method of Example 12, all 3 liters of suspension were used for the 3 Kg of cores.

The coated spheroids were dried and filled into hard gelatine capsules such that each capsule contained 25 mg of triclosan.

The in vitro activities of a range of antimicrobial compounds versus *Helicobacter pylori* were determined by methods based on those of McNulty et al (Antimicrobial Agents and Chemotherapy, 28, 837–838, 1985). The Minimum Inhibitory concentrations for 50% and 90% of the strains used (MIC50 and MIC90), versus each antimicrobial were determined using an agar dilution technique.

The MIC of an antimicrobial agent was defined as that concentration (in mg per liter of agar) at which less than 1 in $10^5$ organisms produced visible colonies.

*Helicobacter pylori* strains were isolated from gastric antrum biopsy specimens taken at routine endoscopy during investigation of upper gastrointestinal symptoms. They were identified as *Helicobacter pylori* by their colonial morphology, gram stain appearance and positive rapid urease test. The organisms were stored in liquid nitrogen before use and subcultured for testing by 48 hour incubation, at 37° C. under 10% carbon dioxide in Tryptone Soya Broth (TSB, OXOID, UK) plus 5% horse serum (Tissue Culture Services, UK).

The first test procedure determined the effectiveness of a range of antimicrobial substances versus 16 to 18 strains of Helicobacter pylori at neutral pH. Freshly prepared Isosensitest Agar of pH 7.2 (Oxoid, UK) supplemented with 10% saponinlysed horse blood was used to prepare a dilution series of each antimicrobial from which agar plates were produced. A multipoint inoculator (Denley-Tech, UK) was used to deliver 1μl of undiluted test culture to the surface of each plate in the dilution series to give approximately $10^6$ cfu/spot. The plates were incubated for three days at 37° C. in a microaerobic atmosphere of 6% oxygen and 10% carbon dioxide.

Table 1 presents test data for the twelve selected antimicrobial agents tested against Helicobacter pylori at neutral pH.

TABLE 1 presents MIC50 and MIC90 values of twelve antimicrobial agents against eighteen isolates of Helicobacter pylori

| Antimicrobial Agent | MIC (mg/l) | | |
|---|---|---|---|
| | MIC50 | MIC90 | Range |
| Triclosan | 1 | 8 | 0.25–16 |
| Tinidazole | 0.5 | 16 | 0.25–16 |
| Cetalkonium Cl | 2 | 4 | 2–4 |
| Cetyl pyridinium Cl | 8 | 8 | 8 |
| Clioquinol | 16 | 16 | 8–16 |
| Hexetidine | 16 | 16 | 8–16 |
| Dichlorphen | 16 | 16 | 8–16 |
| Halquinol | 16 | 16 | 16 |
| 4-Hexylresorcinol | 32 | 32 | 16–32 |
| Hibitane | 32 | 32 | 16–32 |
| PCMX | 32 | 64 | 8–64 |
| Guaiacol | 64 | 64 | 32–128 |

From Table 1 it can be seen that triclosan with an MIC50 of 1 mg/l and an MIC90 of 8 mg/l, and tinidazole with an MIC50 of 0.5 mg/l and an MIC90 of 16 mg/l, demonstrated the greatest activity of the twelve antimicrobial agents tested. A reported MIC90 for bismuth subcitrate at neutral pH is 16 mg/l.

Three of the antimicrobial agents were selected for further evaluation over the pH range of 5 to 8, a range at which Helicobacter pylori survives. The three selected agents were triclosan, clioquinol (5-chloro-7-iodo-8-hydroxy-quinolone) and cetalkonium chloride. Tinidazole was rejected at this stage due to an observed bimodal distribution of MICs. Fifteen of eighteen isolates were sensitive with an MIC of less than 2 mg/l, the other three strains demonstrating evidence of resistance with an MIC of 16 mg/l. This bimodal distribution has previously been reported with metronidazole, another imidazole. In the clinical situation, acquired resistance to the nitroimidazoles can occur in many strains of Helicobacter pylori after only three weeks treatment, therefore, this agent would not be recommended for the treatment of Helicobacter pylori associated gastrointestinal disorders.

The MIC90s of the three selected antimicrobial agents were determined for sixteen to eighteen clinical isolates of Helicobacter pylori over the pH range 5 to 8. In the test procedure, Sorensens phosphate buffer (0.1M) was used to prepare the range of pH values 5, 5.5, 6, 6.5, 7, 7.5 and 8. Oxoid Columbia Agar Base (CM331) was added and the media autoclaved. After cooling to 50° C., 7% Lysed Horse Blood (Tissue Culture Services, UK) was added and media at each pH was used to prepare a range of concentrations of the three selected test antimicrobial agents. To ensure pH stability, a surface pH electrode was used to monitor control plates before, during and at the end of the three day microaerobic incubation.

The MIC90 was determined for each at each pH as described in the previous test procedure.

Tables 2–4 present the test data using the above test procedure.

TABLE 2 presents the effect of pH on the activity (MIC90 mg/l) of triclosan against sixteen isolates of Helicobacter pylori

| pH Value | MIC90 (mg/l) | Range (mg/l) |
|---|---|---|
| 5.0 | 0.25 | 0.06–0.25 |
| 5.5 | 1 | 0.06–1 |
| 6.0 | 1 | 0.12–2 |
| 6.5 | 2 | 0.12–4 |
| 7.0 | 2 | 0.06–4 |
| 7.5 | 2 | 0.06–4 |
| 8.0 | 2 | 0.06–2 |

From Table 2 it can be seen that the MIC90 for triclosan was low at pH 5.0 and unaffected in the range pH 5.5 to 8.0.

TABLE 3 presents the effect of pH on the activity (MIC90 mg/l) of clioquinol against sixteen isolates of Helicobacter pylori

| pH Value | MIC90 (mg/l) | Range (mg/l) |
|---|---|---|
| 5.0 | 2 | 0.5–4 |
| 5.5 | 8 | 2–8 |
| 6.0 | 8 | 2–8 |
| 6.5 | 8 | 0.5–16 |
| 7.0 | 2 | 0.5–4 |
| 7.5 | 2 | 0.5–4 |
| 8.0 | 1 | 0.5–2 |

From Table 3 it can be seen that the activity of clioquinol was only slightly affected by pH. The difference would not be clinically important.

TABLE 4 presents the effect of pH on the activity (MIC90 mg/l) of cetalkonium chloride against eighteen isolates of Helicobacter pylori

| pH Value | MIC90 (mg/l) | Range (mg/l) |
|---|---|---|
| 5.0 | 1 | 0.5–2 |
| 5.5 | 2 | 0.5–2 |
| 6.0 | 2 | 1–4 |
| 6.5 | 4 | 2–4 |
| 7.0 | 4 | 2–4 |
| 7.5 | 4 | 1–4 |
| 8.0 | 2 | 1–8 |

Cetalkonium chloride was largely unaffected by pH over the range 5 to 8.

Of the antimicrobial agents evaluated over a range of pH from 5 to 8, triclosan demonstrated the greatest activity with an MIC90 of 0.25 mg/l (range 0.06–0.25) at pH 5. The activity of the other two agents, clioquinol and cetalkonium chloride, demonstrated similar MIC90 activity profiles across the pH range.

We claim:

1. A method for the treatment of gastrointestinal associated with Heliobacter pylori infection which comprises administering to a patient an orally effective amount for said disorder of triclosan of from 1 to 200 mg.

2. A medicament for use in the method as claimed in claim 1 in unit dosage form, in the form of powders, granules or spheroids packed into sachets, each sachet containing from 1 to 100 mg triclosan.

3. A medicament as claimed in claim 2 wherein each unit contains 10 to 60 mg triclosan.

4. A medicament for use in the method as claimed in claim 1 in unit dosage form, in the form of tablets or capsules, each unit containing 1 to 100 mg triclosan.

5. A medicament as claimed in claim 4 wherein each unit contains 10 to 60 mg triclosan.

6. A medicament for use in the method as claimed in claim 1 in the form of a liquid containing 1 to 100 mg of triclosan in 5 to 20 ml.

7. A medicament for use in the method as claimed in claim 1 in a solid unit dosage form comprising 200 to 600 mg of alginic acid and/or a sodium, potassium or magnesium salt thereof; 50 to 250 mg of a sodium or potassium carbonate or bicarbonate salt; 1 to 100 mg triclosan; and 0 to 100 mg calcium carbonate.

8. A medicament as claimed in claim 7 wherein the weight of triclosan is 10 to 60 mg.

9. A medicament as claimed in claim 7 which additionally includes a pharmaceutically acceptable solid carboxylic acid or an acid salt thereof in sufficient amount to neutralise between one quarter and all of the carbonate and/or bicarbonate of the composition.

10. A medicament as claimed in claim 9 wherein the acid is citric acid.

11. An aqueous medicament for use in the method as claimed in claim 1 comprising 0.1 to 2% w/v triclosan; 1 to 8% w/v sodium or potassium alginate; 1.3 to 6.5% w/v of a sodium or potassium carbonate or bicarbonate salt; 0.5 to 4% w/v calcium carbonate; and optionally 0.3 to 1.7% w/v carbomer.

12. A medicament for use in the method as claimed in claim 1 in the form of granules or spheroids comprising triclosan and optionally a pharmaceutically acceptable carrier, coated with a mucoadherent polymer selected from carboxymethylcellulose, sodium carboxymethylcellulose, carbomer, tragacanth, sodium alginate, methylcellulose, hydroxyethylcellulose, poly(ethylene oxide) and hydroxy propylmethylcellulose.

13. A medicament as claimed in claim 8 which additionally includes a pharmaceutically acceptable solid carboxylic acid or an acid salt thereof in sufficient amount to neutralise between one quarter and all of the carbonate and/or bicarbonate of the composition.

14. A method for the treatment of gastrointestinal disorders associated with *Heliobacter pylori* infection which comprises administering to a patient an orally effective amount for said disorder of triclosan of from 1 to 100 mg.

15. A method for the treatment of gastrointestinal disorders associated with *Heliobacter pylori* infection as claimed in claim 14 and which comprises administering to a patient an orally effective amount for treating said disorders of triclosan and wherein said disorder is a peptic ulcer.

16. A method for the treatment of gastrointestinal disorders associated with *Heliobacter pylori* infection as claimed in claim 14 and which comprises administering to a patient an orally effective amount for treating said disorders of triclosan and wherein said disorder is gastritis.

17. A method for the treatment of gastrointestinal disorders associated with *Heliobacter pylori* infection as claimed in claim 14 and which comprises administering to a patient an orally effective amount for treating said disorders of triclosan and wherein said disorder is a peptic ulcer and said triclosan is contained in a medicament in solid unit dosage form comprising 200 to 600 mg of alginic acid and/or a sodium, potassium or magnesium salt thereof; 50 to 250 mg of a sodium or potassium carbonate or bicarbonate salt; 1 to 100 mg of triclosan; and 0 to 100 mg calcium carbonate.

18. A method for the treatment of gastrointestinal disorders associated with *Heliobacter pylori* infection as claimed in claim 14 and which comprises administering to a patient an orally effective amount for treating said disorders of triclosan and wherein said disorder is a peptic ulcer and said triclosan is contained in a medicament in solid unit dosage form comprising 200 to 600 mg of alginic acid and/or a sodium, potassium or magnesium salt thereof; 50 to 250 mg of a sodium or potassium carbonate or bicarbonate salt; 1 to 100 mg of triclosan; and 0 to 100 mg calcium carbonate; and
  which medicament additionally includes a pharmaceutically acceptable solid carboxylic acid or an acid salt thereof in sufficient amount to neutralize between one quarter and all of the carbonate and/or bicarbonate of the composition.

19. A method for the treatment of gastrointestinal disorders associated with *Heliobacter pylori* infection as claimed in claim 14 and which comprises administering to a patient an orally effective amount for treating said disorders of triclosan and wherein said disorder is a peptic ulcer, and said triclosan is contained in an aqueous medicament comprising 0.1 to 2% w/v triclosan; 1 to 8% w/v sodium or potassium alginate; 1.3 to 6.5% w/v of a sodium or potassium carbonate or bicarbonate salt; 0.5 to 4% w/v calcium carbonate; and optionally 0.3 to 1.7% w/v carbomer.

20. A method for the treatment of gastrointestinal disorders associated with *Heliobacter pylori* infection as claimed in claim 14 and which comprises administering to a patient an orally effective amount for treating said disorders of triclosan and wherein said disorder is gastritis and said triclosan is contained in a medicament in solid unit dosage form comprising 200 to 600 mg of alginic acid and/or a sodium, potassium or magnesium salt thereof; 50 to 250 mg of a sodium or potassium carbonate or bicarbonate salt; 1 to 100 mg of triclosan; and 0 to 100 mg calcium carbonate.

21. A method as claimed in claim 1 wherein the patient is a human patient.

22. A method for the treatment of gastrointestinal disorders associated with *Heliobacter pylori* infection as claimed in claim 14 and which comprises administering to a patient an orally effective amount for treating said disorders of triclosan and wherein said disorder is gastritis and said triclosan is contained in a medicament in solid unit dosage form comprising 200 to 600 mg of alginic acid and/or a sodium, potassium or magnesium salt thereof; 50 to 250 mg of a sodium or potassium carbonate or bicarbonate salt; 1 to 100 mg of triclosan; and 0 to 100 mg calcium carbonate; and
  which medicament additionally includes a pharmaceutically acceptable solid carboxylic acid or an acid salt thereof in sufficient amount to neutralize between one quarter and all of the carbonate and/or bicarbonate of the composition.

23. A method for the treatment of gastrointestinal disorders associated with *Heliobacter pylori* infection as claimed in claim 14 and which comprises administering to a patient an orally effective amount for treating said disorders of triclosan and wherein said disorder is gastritis, and said triclosan is contained in an aqueous medicament comprising 0.1 to 2% w/v triclosan; 1 to 8% w/v sodium or potassium alginate; 1.3 to 6.5% w/v of a sodium or potassium carbonate or bicarbonate salt; 0.5 to 4% w/v calcium carbonate; and optionally 0.3 to 1.7% w/v carbomer.

* * * * *